United States Patent [19]

Rabban

[11] Patent Number: 5,514,077
[45] Date of Patent: May 7, 1996

[54] SURGICAL RETRACTOR

[76] Inventor: Philipp Rabban, P.O. Box 447, Hallandale, Fla. 33008

[21] Appl. No.: 270,648

[22] Filed: Jul. 5, 1994

[51] Int. Cl.⁶ ................................................. A61B 17/02
[52] U.S. Cl. ...................... 600/226; 606/191; 16/110 R; 600/201; 600/204
[58] Field of Search .................. 128/20, 17, 18, 128/12, 13, 3; 606/191, 198; 297/57–58; 16/110

[56] References Cited

U.S. PATENT DOCUMENTS

| | | | |
|---|---|---|---|
| 1,025,265 | 5/1912 | Grindle | 128/17 |
| 2,075,534 | 3/1937 | McCormack | 128/17 |
| 3,858,578 | 1/1975 | Milo | 128/20 |
| 4,038,719 | 8/1977 | Bennett | 16/110 R |
| 4,122,844 | 10/1978 | Rabban | 128/20 |
| 5,125,130 | 6/1992 | Stanish | 16/110 R |
| 5,351,680 | 10/1994 | Jung | 128/20 |
| 5,375,591 | 12/1994 | Mouret | 128/20 |
| 5,379,758 | 1/1995 | Snyder | 128/20 |

FOREIGN PATENT DOCUMENTS

| | | | |
|---|---|---|---|
| 2475885 | 8/1981 | France | 128/20 |
| 1421320 | 9/1988 | U.S.S.R. | 128/20 |
| 1690704 | 11/1991 | U.S.S.R. | 128/20 |

Primary Examiner—Richard J. Apley
Assistant Examiner—Kelly McGlashen
Attorney, Agent, or Firm—M. K. Silverman

[57] ABSTRACT

A push-type hand-held surgical retractor definable in terms of an xyz Cartesian coordinate system, includes a substantially flat retaining element having a primary surface in a yz plane and a secondary surface, substantially normal thereto, in an xy plane. The retractor also includes a curved elongated rigid shaft having first and second ends and having a gradual x-axis curve in both the xy plane and an accentuated y-axis curve in the xy and yz planes, the curved shaft having, at the first end, an arched portion having the y-axis curve, in which the first end integrally depends from an upper side of the secondary surface of the retaining element. The retractor further includes an ellipsoidal loop-like gripping element integrally depending from the second end of the curved elongate shaft.

7 Claims, 2 Drawing Sheets

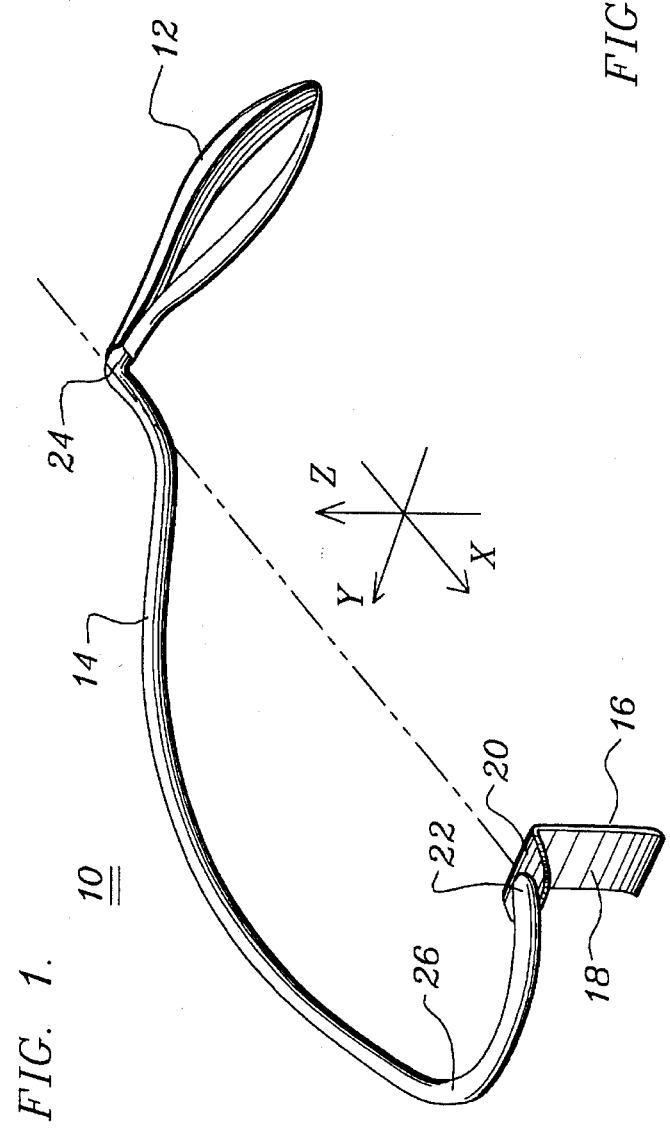
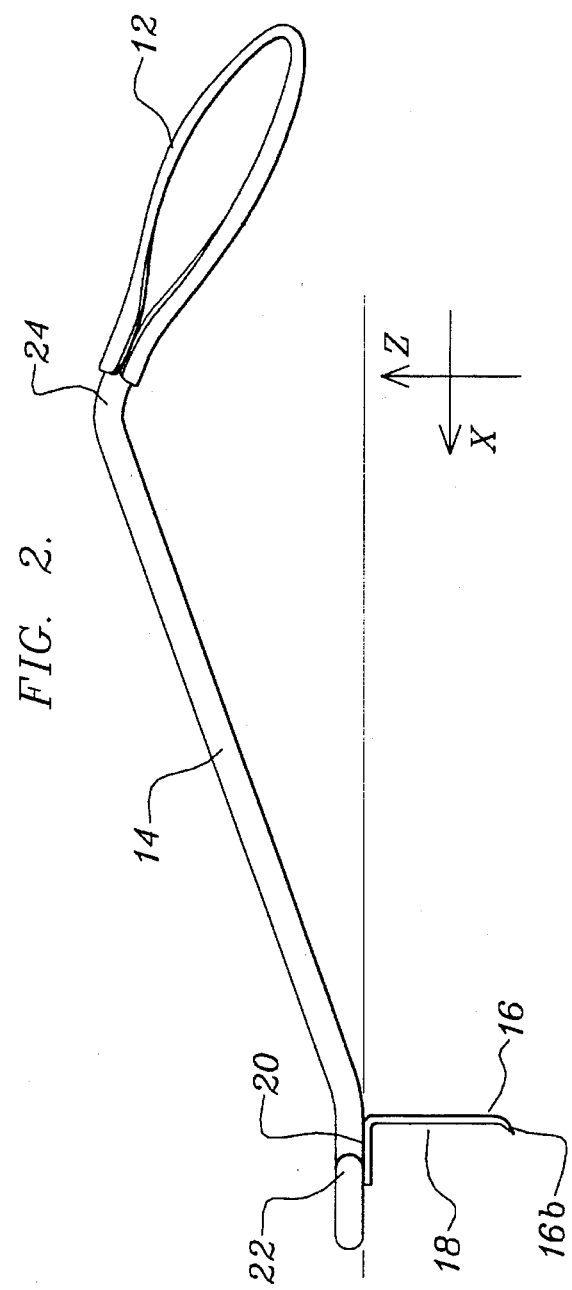

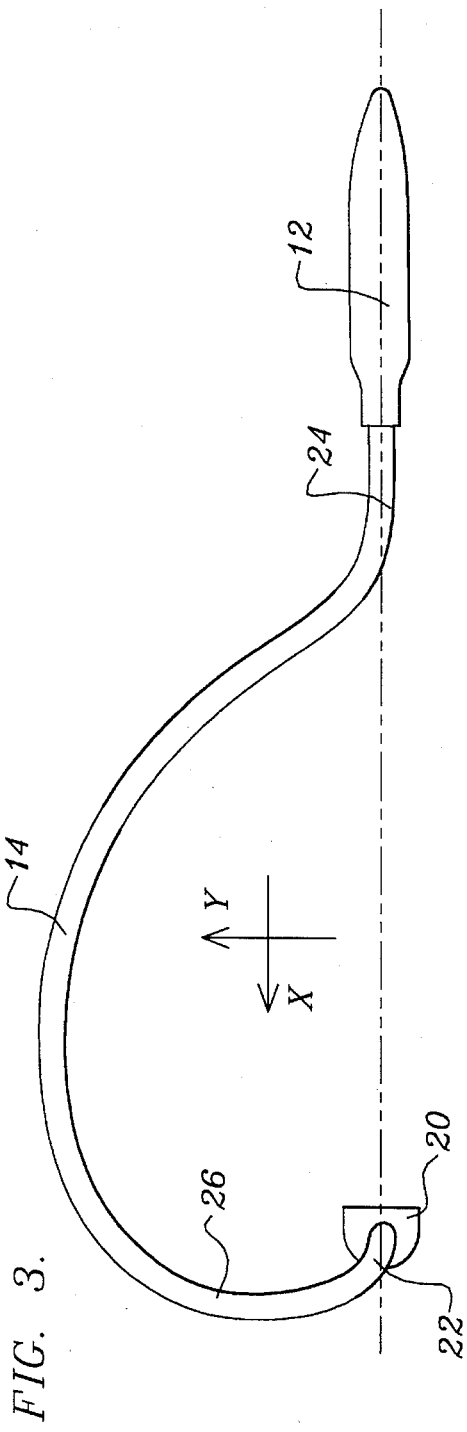
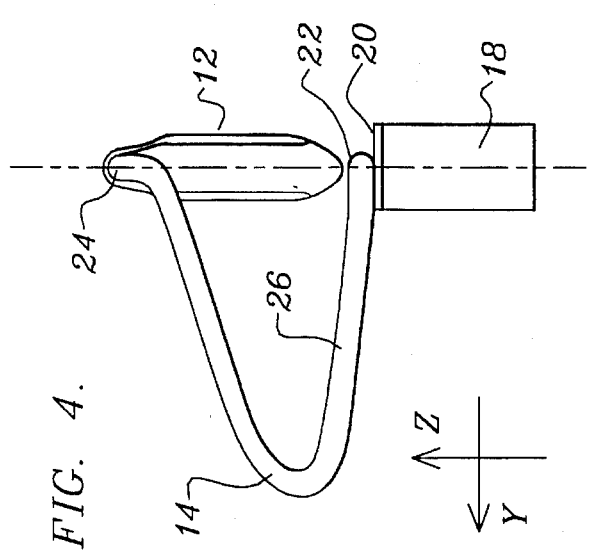

SURGICAL RETRACTOR

BACKGROUND OF THE INVENTION

The present invention relates to the area of surgical retractors and, particularly, to surgical retractors having primary utility when the anatomical structures to be retracted are located at the same side of the operating physician.

Surgical retractors are used to hold a surgical incision open during a surgical procedure. At present, retraction is effected by the pulling of a retractor by an assistant as is located either opposite or beside the surgeon, or by means of a self-retaining retractor. There exist numerous disadvantages that are inherent in present methods and means for retraction. For example, when the assistant is positioned beside the surgeon and is pulling a retractor, the assistant cannot, for the most part, see what the surgeon is doing. Moreover, the act of continuous pulling by the assistant typically proves to be very fatiguing. The consequences thereof are, those of inefficiency, inaccuracy, and the potential for additional trauma to the patient.

In those conditions to retract the site opposite to the assistant in which the assistant is positioned at the opposite side of the surgeon, it has been found that the pulling of the retractor by the assistant is even more fatiguing because the assistant's arm is fully extended, this entailing resulting harm to the respiration of the patient. However, when the assistant is positioned along side of the surgeon, although this is a more convenient location to the assistant, this position has been found to hamper free movement on the part of the operator surgeon and risky for the patient since he is unable to see the essential work of the surgeon or the conditions that he is feeling.

Furthermore, in any case, the assistant's arm will frequently find itself resting upon the patient's body and thereby impairing his respiration.

The self-retaining retractor, which is typically bilateral in its action, provides retraction on the side at which it is not needed as well at the side at which it is needed. As such, the resultant forces and pressure from the self-retaining retractor often operate to induce unnecessary trauma to the patient. Moreover, the self-retaining retractor must often be supplemented with manual retraction means and always requires a longer incision.

The instant invention represents an improvement of my surgical retractor reflected in U.S. Pat. No. 4,122,844 (1978). As such, the present invention, like that taught in my said 1978 U.S. Patent, is of utility primarily in the retraction of the ipsilateral relative to the surgeon and in accomplishing sutures of incisions in connection therewith. It is of secondary application in the retraction of cranial and caudal portions of an incision.

The present invention may, therefore, be understood as yet a further improvement in my inventions relative to the subject of pushed or pushable surgical retractors.

SUMMARY OF THE INVENTION

The present invention is a push-type hand-held surgical retractor definable in terms of an xyz Cartesian coordinate system. The retractor, more particularly, includes a substantially flat retaining element having a primary surface in a yz plane and a secondary surface, substantially normal thereto, in an xy plane. The retractor also includes a curved elongated rigid shaft having first and second ends and having a gradual x-axis curve in both the xy plane and an accentuated y-axis curve in the xy and yz planes, said curved shaft having, at said first end thereof, an arched portion comprising said y-axis curve, in which said first end integrally depends from an upper side of said secondary surface of said retaining element. The retractor further includes an ellipsoidal loop-like gripping means integrally depending from said second end of said curved elongate shaft.

It is an object of the invention to provide a surgical retractor particularly adapted to function by pushing, as opposed to pulling.

It is another object to provide a surgical retractor of the above type that is less fatiguing to a surgical assistant to utilize than a conventional pulling retractor.

It is a further object of the invention to provide a retractor of a type that will enable a surgical assistant to function in a manner that will not impair the visibility of the surgeon.

It is a yet further object to provide a surgical retractor of the above type that will reduce the need for the assistant to lean on the patient during a surgical procedure.

It is a still further object of the invention to provide a surgical retractor that will reduce awkwardness associated with prior art retractors and will reduce the potential for trauma caused thereby to the patient when it is used at a site opposite to the retracting assistant.

The above and yet other objects and advantages of the present invention will become apparent from the hereinafter set forth Brief Description of the Drawings, Detailed Description of the Invention, and Claim appended herewith.

BRIEF DESCRIPTION OF THE DRAWINGS

FIG. 1 is a perspective view of the inventive retractor relative to an xyz coordinate system.

FIG. 2 is a side view thereof corresponding to the xz plane of the xyz coordinate system.

FIG. 3 is a top view of the invention, corresponding to the xy plane.

FIG. 4 is a front view thereof, corresponding to the yz plane.

DETAILED DESCRIPTION OF THE INVENTION

There is, with reference to the perspective view of FIG. 1 shown the instant inventive surgical retractor 10. Also shown therein is an xyz Cartesian coordinate system which, as is set forth below, is employed to more particularly define the invention. As an aspect of this definition it is to be understood that the x-axis shown in FIG. 1 is hereinafter alternatively referred to as the pushing axis of the retractor in that it is along this axis that the surgical assistant applies forward force against gripping means or handle 12 which, therefrom, is communicated through a curved rigid shaft 14 and, therefrom, to a flat retaining element 16. This element, as may be also seen with reference to FIG. 2, consists of a primary surface 18 which exists within a yz plane of said xyz coordinate system, formed at the extremity of which is a conventional lip portion 16b, and a secondary surface 20 (see also FIG. 3) which exists in a xy plane.

As may be noted with reference to FIGS. 1 thru 4, said curved shaft 14 of the surgical retractor includes a first end 22 and a second end 24. It is to be further noted that the curved geometry of shaft 14 is defined by a gradual x-axis curve (see FIG. 3) and an accentuated y-axis curve in the xy and yz planes (see FIGS. 3 and 4 respectively). As may be seen in these figures, the curved shaft 14 includes an arched portion 26, the beginning of which corresponds to said first end 22 of shaft 14.

As may be more particularly seen in the figures, arched portion 26 depends from upper side of said secondary surface 20 of said retaining element 16. As may be noted in FIGS. 3 and 4, the relative curvature of said arched portion 26 is substantially greater in the yz plane than in the xy plane. Further, said gradual y-axis curve of shaft 14 occurs only in the xy plane in that, for example, in the yz plane of FIG. 4, the degree of change of curvature in the yz plane is much greater. The combination of said curves, and rate of change of the curvature of shaft 14, may be more fully seen with reference to the perspective of FIG. 1. Therein, and with reference to the side view of FIG. 2, it may be noted that the overall curvature of rigid shaft 14 is one which increases, substantially constantly, in z-axis elevation while defining a ladle-like curve in the xy plane (top view) of FIG. 3. Also, the acute curvature of arched portion 26 within the y-axis is shown in the yz plane (front view) of FIG. 4. Therein, as well as in the side view of FIG. 2, it may be noted that the z-axis elevation of handle 12 is completely above that of retaining element 18.

It may, with particular reference to the side view of FIG. 2, be seen that handle 12 is defined by a band-like loop which, in the xz plane of FIG. 2, defines an ellipse having a major-to-minor axis ratio in the range of between about three-to-one and about six-to-one. As may be further noted in FIG. 2, said handle 12 depends integrally from said second end 24 of shaft 14. It has been found that a band-like loop, when the major axis thereof defines an obtuse angle in the range of 115 to 155 degrees relative to the xz plane axis of shaft 14, will produce an ergometric effect such that the maximum mechanical advantage of the muscle power of the surgical assistant is applied to the primary surface 18 of flat retaining element 16. This ergometric relationship between handle 12, curved shaft 14 and flat retaining element 18 thereby produces the various anti-fatiguing and patient safety characteristics set forth in the objects of the invention recited above.

The ergometric operation of the instant invention is also definable in terms of the ratio of the x-axis length of the curved shaft 14 to the length of the major axis of the handle 12. This relationship may, with reference to FIG. 2, be seen to that of a ratio which is in the range of about two-to-one to about four-to-one. A further ergometric relationship which enables the invention to effect its intended purposes is that of the ratio of the z-axis length of retaining element 16 to the x-axis length of the handle which, as may be seen in FIG. 2, is in the range of about one-to-two to about two-to-one.

In view of the above it is to be appreciated that there is provided a push-type instrument that is lighter than other known prior art of retractors and is more effective for the various purposes for which it is intended, as are more particularly set forth above.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

Having thus described my invention what I claim as new, useful and non-obvious and, accordingly, secure by Letters Patent of the United States is:

1. A hand-held surgical retractor definable in terms of an xyz Cartesian coordinate system, the retractor comprising:

a). a substantially flat retaining element having a primary surface in a yz plane and a secondary surface, substantially normal thereto, in an xy plane, and a midline defined by the intersection of an xz plane normal to both said primary and secondary surfaces;

b). a curved elongated rigid shaft having a first end integrally depending from an upper side of said secondary surface of said retaining element and lying in said xz plane, a second end opposite said first end and lying in the xz plane, a first arched portion adjacent to said first end comprising an accentuated curve in the xy plane initiating in a direction normal to said primary surface and away from the user, said first arched portion smoothly adjacent a second arched portion, said second arched portion terminating at said second end and comprising a reversed gradual curve in the xy plane, said first and second arched portions coincident with a rise in the xz plane; and c). gripping means proportioned for engagement by all fingers of one hand of user of said retractor, said gripping means integrally depending from said second end of said curved elongated shaft and lying in said xz plane.

2. The surgical retractor as recited in claim 1, in which said gripping means comprises:

a band in the form of a loop, said loop defining, in an xz plane, substantially an ellipse having a major-to-minor axis ratio of between about three-to-one to about four-to-one, said loop integrally depending from said second end of said curved shaft at an end of said loop corresponding to an end of the major axis of said ellipse.

3. The surgical retractor as recited in claim 2, in which the ratio of the x-axis of the length of said curved shaft, in the xz plane relative to the major axis length of said loop of gripping means, is in the range of about two-to-one to about four-to-one.

4. The surgical retractor as recited in claim 3, in which the ratio of the z-axis length of said retaining element, in the xz plane, to the x-axis length of said gripping means is in the range of about one-to-two to about two-to-one.

5. The surgical retractor as recited in claim 4 in which the z-axis elevation of said gripping means is above that of said retaining element.

6. The surgical retractor as recited in claim 5 in which said major axis to said loop of said gripping means defines an obtuse angle relative to the xz plane axis of said shaft in the range of 115 to 155 degrees.

7. The surgical retractor as recited in claim 1, in which said primary surface of said retaining element includes a y-axis lip depending integrally from said surface in a direction opposite of said gripping means.

* * * * *